United States Patent [19]
Nakajima et al.

[11] Patent Number: 4,915,813
[45] Date of Patent: Apr. 10, 1990

[54] OXYGEN CONCENTRATION DETECTING DEVICE

[75] Inventors: Toyohei Nakajima; Toshiyuki Mieno; Yasuhiro Toyoda; Akira Kato; Haruo Horiuchi; Toru Yano, all of Wako, Japan

[73] Assignee: Honda Giken Kogyo Kabushiki Kaisha, Tokyo, Japan

[21] Appl. No.: 281,713

[22] Filed: Dec. 9, 1988

[30] Foreign Application Priority Data

Dec. 9, 1987 [JP] Japan ................................. 62-312670
Dec. 28, 1987 [JP] Japan ................................. 62-332843
May 30, 1988 [JP] Japan ................................. 63-71489
Jun. 30, 1988 [JP] Japan ................................. 63-162855

[51] Int. Cl.$^4$ ........................................... G01N 27/58
[52] U.S. Cl. ...................................... 204/406; 60/276; 123/489
[58] Field of Search ............... 204/406, 410, 412, 425, 204/15; 60/276; 123/489

[56] References Cited
U.S. PATENT DOCUMENTS

| | | | |
|---|---|---|---|
| 3,791,937 | 2/1974 | Besson et al. ................. | 204/412 X |
| 4,615,787 | 10/1986 | Yamada et al. ................ | 204/406 |
| 4,724,814 | 2/1988 | Mieno et al. .................. | 123/479 |
| 4,759,827 | 7/1988 | Okada et al. .................. | 204/1 T |
| 4,787,966 | 11/1988 | Nakajima et al. .............. | 204/406 |

Primary Examiner—G. L. Kaplan
Attorney, Agent, or Firm—Pollock, Vande Sande & Priddy

[57] ABSTRACT

An oxygen concentration detecting device includes at least one oxygen concentration detecting element formed by an oxygen-pumping element and a cell element, composed of an oxygen ion-conductive wall, separating a pair of electrodes. The oxygen-pumping element and cell element define a gas diffusion chamber. A current detecting resistance forms a series circuit with the oxygen-pumping element. A voltage applying circuit applies to the series circuit an output voltage corresponding to the difference between a voltage between the electrodes of the cell element and a first reference voltage. An output detecting circuit outputs a voltage signal corresponding to a value of pumping current flowing through the resistance. An operational amplifier has a non-inverting input terminal supplied with a second reference voltage, an inverting input terminal connected to one end of the resistance, and an output terminal connected to the other end of the resistance. The output detecting circuit detects a first voltage at the one end of the resistance and a second voltage at the other end and outputs the voltage signal corresponding to the difference between the detected first and second voltages. The output detecting circuit corrects the voltage signal based upon the first and second voltages which are obtained in a state where no pumping current is supplied to the resistance. Electrodes of the oxygen-pumping element and the cell element are connected together within the gas diffusion chamber or within the basic body of the sensor body.

12 Claims, 10 Drawing Sheets

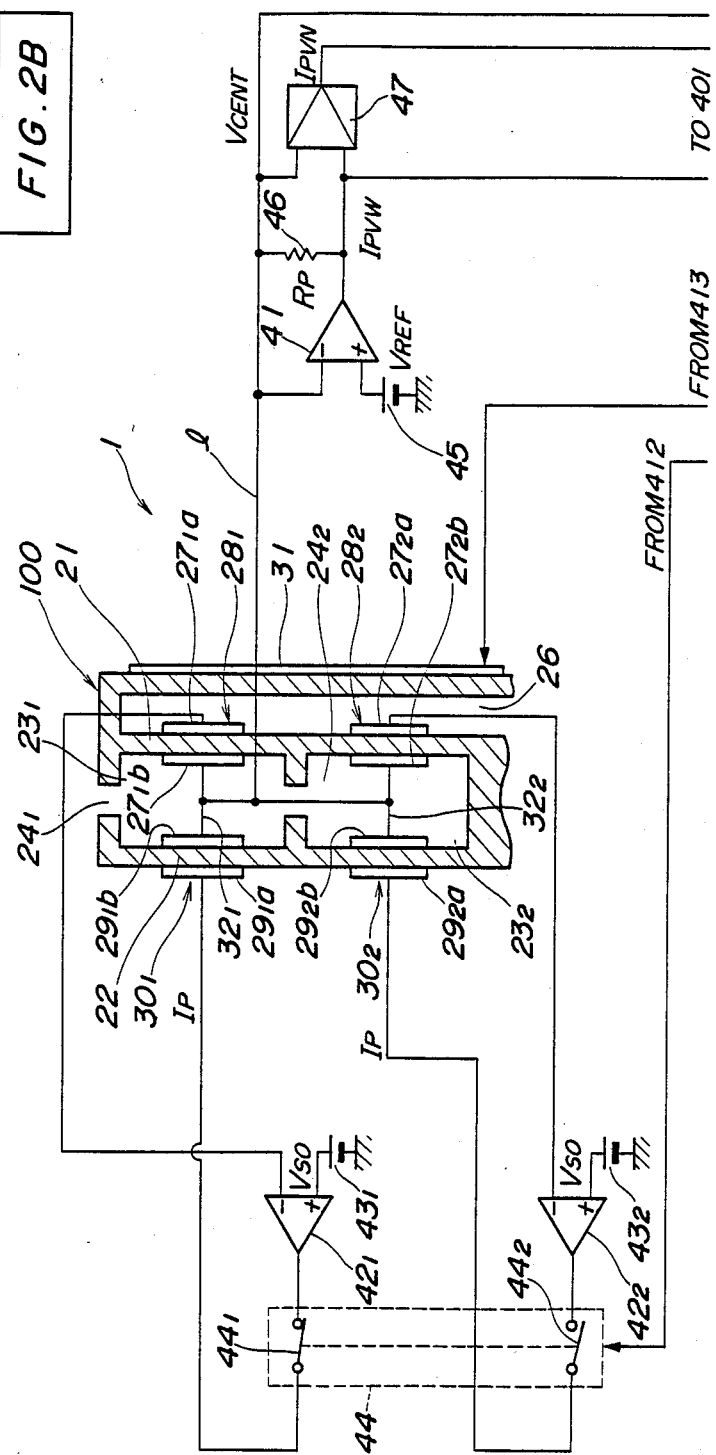

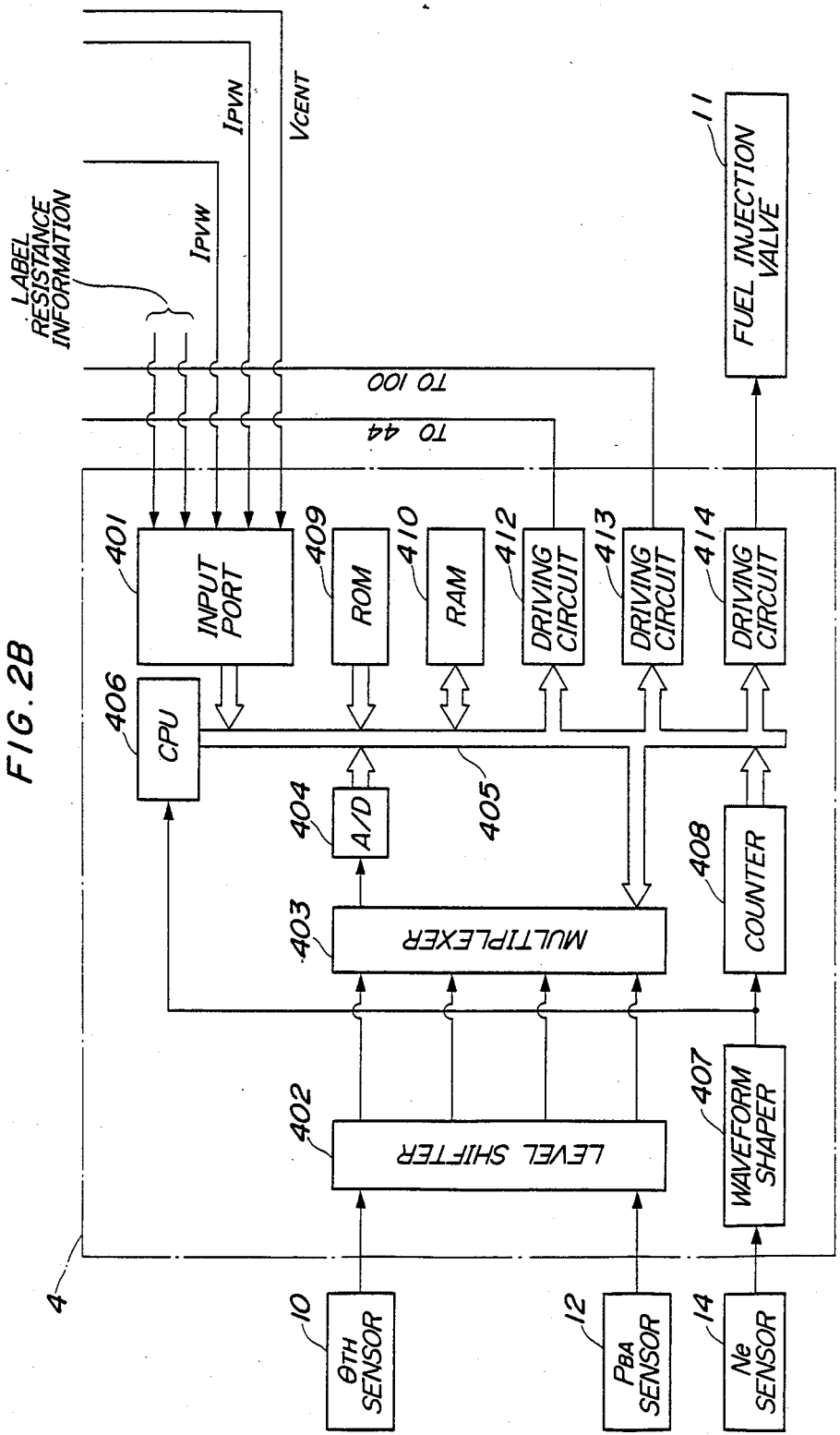

OXYGEN CONCENTRATION DETECTING DEVICE

BACKGROUND OF THE INVENTION

This invention relates to an oxygen concentration detecting device which generates an output proportional to the concentration of oxygen in exhaust gases from an internal combustion engine.

An air-fuel ratio control system for an internal combustion engine is known, e.g., from Japanese Patent Publication (Kokoku) No. 55-3533, which senses oxygen concentration in exhaust gases from the engine, and controls the air-fuel ratio of a mixture supplied to the engine to a desired value in a feedback manner responsive to the detected concentration value, to thereby purify the exhaust gases and decrease the fuel consumption.

The above-mentioned oxygen concentration detecting device for use in an air-fuel ratio control system includes a type which generates an output proportional to the concentration of oxygen contained in the exhaust gases, i.e., the air-fuel ratio of the exhaust gases. An oxygen concentration detecting device of this type is disclosed, e.g., in Japanese Provisional Patent Publication (Kokai) No. 59-192955, which comprises an oxygen-pumping element and a cell element, each being composed of a plate-like member formed of a solid electrolytic material having oxygen ion-conductivity, and a couple of electrodes attached to opposite side surfaces of the plate-like member. A gas diffusion chamber is partly defined by one of the electrodes of each of the oxygen-pumping element and the cell element. A gas to be examined is introduced into the gas diffusion chamber through a gas-introducing slit. An air chamber into which the atmosphere is introduced is provided adjacent the cell element, with the other of the coupled electrodes of the cell element facing the interior of the air chamber.

According to the disclosed oxygen concentration detecting device, in order to maintain the concentration of oxygen present within the gas diffusion chamber at a predetermined value (e.g., 0), a voltage developed across the cell element is compared with a predetermined reference value, and pumping current is caused to flow between the two electrodes of the oxygen-pumping element in response to the result of the comparison. The value of the pumping current is outputted as an output proportional to the oxygen concentration in the gas to be examined.

To detect the pumping current, a current detecting resistance is used, which is connected in series to the oxygen-pumping element, voltages at opposite ends of which are utilized to obtain a voltage representing the pumping current.

According to an oxygen concentration detecting device of the proportional-output type as described above, as distinct from the so-called $\alpha=1$ type oxygen concentration sensor whose output voltage abruptly changes as the air-fuel ratio changes across the stoichiometric air-fuel ratio, the pumping current $I_p$ changes linearly as the air-fuel ratio changes on the rich side or on the lean side with respect to the stoichiometric ratio, without abruptly changing in the vicinity of the stoichiometric air-fuel ratio, as shown in FIG. 1. The detection of the air-fuel ratio utilizes the linear relationship between the pumping current and the air-fuel ratio. However, in actuality, as stated before, the air-fuel ratio is determined from a voltage outputted from the detection system including the current detecting resistance, it is requisite to enhance the accuracy of conversion of the pumping current $I_p$ into the voltage in order to accurately determine the air-fuel ratio.

In the conventional device, the system for detecting the pumping current $I_p$ is formed by part of a control circuit which controls the supply of pumping current $I_p$ to the oxygen-pumping element. Any circuit error may cause noise contained in the pumping current signal, which impedes accurate detection of the air-fuel ratio and hence degrades the detection accuracy.

Further, in the case where the oxygen concentration detecting device is arranged in a place undergoing high level noise, such as external noise in ignition pulses of an internal combustion engine, it is difficult to accurately determine changes in voltages at the opposite ends of the current detecting resistance, which also forms a factor for degraded detection accuracy.

Also, in the case where the air-fuel ratio control is effected by the use of an oxygen concentration sensor of the proportional-output type in an internal combustion engine equipped with a three-way catalytic converter arranged in the exhaust system, the catalytic converter has the maximum conversion efficiency when the air-fuel ratio of a mixture supplied to the engine assumes a stoichiometric ratio (e.g., 14.7). Therefore, the air-fuel ratio is controlled so as to become equal to the stoichiometric ratio by means of feedback control responsive to the oxygen concentration sensor. Specifically, the feedback control is effected in response to an air-fuel ratio signal corresponding to the difference between the actual air-fuel ratio and the stoichiometric ratio. However, when the actual air-fuel ratio is close to the stoichiometric ratio, the difference between the two ratios is small, which necessitates amplifying the difference so as to secure a required degree of accuracy of the air-fuel ratio control. However, if the amplification degree or factor is set to too large a value, there can occur saturation of the air-fuel ratio signal, thus making it difficult to set the amplification degree.

Moreover, in the conventional oxygen concentration detecting device, the negative pole electrode of the cell element and the electrode of the oxygen-pumping element which are disposed in the gas diffusion chamber are grounded by way of respective long lead wires extending separately from each other. As a result, there is a problem of fluctuation or variation of the output of the sensor, i.e., the pumping current. This has been a bar to employment of a proportional-output type oxygen concentration sensor in an air-fuel ratio control system.

To be specific, since the grounding lead wires are disposed to separately extend over a long distance to the electrical system such as a control circuit where they are grounded, there occurs a difference in potential between the sensor body and the electrical system, i.e., a difference in potential between the two electrodes in the gas diffusion chamber. Especially, since the sensor body of the oxygen concentration detecting device is mounted in the exhaust system of the engine which is remote from the electrical system, the above potential difference cannot be prevented even if the two electrodes are grounded at the same point. Further, since feedback control is effected so as to maintain the voltage across the cell element constant, such potential difference may cause self-oscillation of the feedback system, in a high frequency range in particular. This causes fluctuations in the output from the detecting device, even if the detected air-fuel ratio remains the same. That is, it causes fluctuations in the pumping current, resulting in degraded detection accuracy.

SUMMARY OF THE INVENTION

It is an object of the invention to provide an oxygen concentration detecting device which is capable of providing an accurate output indicative of the pumping current flowing in the oxygen-pumping element.

It is a further object of the invention to provide an oxygen concentration detecting device which is capable of providing an accurate output indicative of the pumping current even when the air-fuel ratio is in the vicinity of the stoichiometric ratio.

Another object of the invention is to provide an accurate output indicative of the pumping current even when a noise factor attributable to circuit error, external noise, etc. is present in the device.

The above and other objects, features, and advantages of the invention will be more apparent from the ensuing detailed description taken in conjunction with the accompanying drawings.

According to a first aspect of the invention, there is provided an oxygen concentration detecting device including at least one oxygen concentration detecting element formed by an oxygen-pumping element and a cell element, each of the oxygen-pumping element and the cell element composed of a wall of a solid electrolytic material having oxygen ion-conductivity, and a pair of electrodes having the wall interposed therebetween, the oxygen-pumping element and the cell element defining a gas diffusion-limiting zone, a current detecting resistance connected in series to the oxygen-pumping element and cooperating therewith to form a series circuit, the current detecting resistance having one end and the other end, voltage applying means for applying an output voltage corresponding to the difference between a voltage developed between the electrodes of the cell element and a first predetermined reference voltage to the series circuit formed by the oxygen-pumping element and the current detecting resistance, and output detecting means for outputting in the form of a voltage signal a value of pumping current flowing through the current detecting resistance.

The oxygen concentration detecting device of the first aspect of the invention is characterized by an improvement comprising an operational amplifier circuit having a non-inverting input terminal supplied with a second predetermined reference voltage, an inverting input terminal connected to the one end of the current detecting resistance, and an output terminal connected to the other end of the current detecting resistance, and wherein the output detecting means detects a first voltage at the end of the current detecting resistance and a second voltage at the other end of same and outputs the voltage signal corresponding to the difference between the detected first and second voltages.

The oxygen concentration detecting device may include converter means for converting the first voltage and the second voltage, respectively, to a first digital value and a second digital value, and calculating means for calculating the difference between the first and second digital values.

According to a second aspect of the invention, the oxygen concentration detecting device is characterized by an improvement comprising an operational amplifier circuit having a non-inverting input terminal supplied with a second predetermined reference voltage, an inverting input terminal connected to the one end of the current detecting resistance, and an output terminal connected to the other end of the current detecting resistance, and wherein the output detecting means includes correction means for correcting the voltage signal on the basis of the first voltage at the one end of the current detecting resistance and the second voltage at the other end of same which are obtained in a state where no pumping current is supplied to the current detecting resistance.

The oxygen concentration detecting device may include heater means for heating the oxygen-pumping element and the cell element, and wherein the state where no pumping current is supplied includes a state where the heater means is inactivated.

The oxygen concentration detecting device further may include differential amplifier means for amplifying a difference between the first and second voltages, and wherein the correcting means corrects the voltage signal by a correction amount corresponding to a difference between the first voltage and the amplified difference from the amplifier means which are obtained in the state where no pumping current is supplied.

The voltage signal may be the difference between the amplified difference and a reference voltage of the first voltage, the correcting means subtracting the correction amount from the difference.

The reference voltage of the first voltage may be the first voltage obtained when the pumping current is zero there exists no offset in the operational amplifier circuit.

The correcting means may correct the voltage signal when the pumping current assumes a value falling within a predetermined small value range including zero.

According to a third aspect of the invention, there is provided an air-fuel ratio detecting device for an internal combustion engine, the device being arranged in an exhaust system of the engine and including at least one oxygen concentration detecting element formed by an oxygen-pumping element and a cell element, each of the oxygen-pumping element and the cell element composed of a wall of a solid electrolytic material having oxygen ion-conductivity, and a pair of electrodes having the wall interposed therebetween, current applying means for applying pumping current to the oxygen-pumping element to cause the pumping current to flow between the electrodes thereof, and controlling the pumping current to a value substantially proportional to the difference between actual oxygen concentration in exhaust gases from the engine and a predetermined reference value of the oxygen concentration, and signal generating means for generating a signal indicative of an air-fuel ratio of the exhaust gases corresponding to the controlled value of the pumping current.

The air-fuel ratio detecting device of the invention is characterized by an improvement wherein the signal generating means comprises voltage generating means for generating an output voltage corresponding to the controlled value of the pumping current, voltage amplifying means for amplifying the output voltage from the voltage generating means, and determining means for increasing the amplification factor of the voltage amplifying means assumed when an output voltage from the voltage amplifying means falls within a predetermined range corresponding to a stoichiometric air-fuel ratio and its vicinity, to a value larger that a value assumed when the output voltage from the voltage amplifying means falls out of the predetermined range, and determining the air-fuel ratio in the exhaust gases from the output voltage from the voltage amplifying means.

The voltage amplifying means may comprise a first voltage amplifier, and a second voltage amplifier having a larger amplification factor than that of the first voltage amplifier, the determining means determining the air-fuel ratio in the exhaust gases from an output voltage from the second voltage amplifier when the output voltage from the second voltage amplifier falls within a predetermined range, and determining the air-fuel ratio in the exhaust gases from an output voltage from the first voltage amplifier when the output voltage from the second voltage amplifier falls out of the predetermined range.

According to a fourth aspect of the invention, there is provided an oxygen concentration detecting device including a basic body having at least two walls formed of a solid electrolytic material having oxygen ion-conductivity, and at least one gas diffusion chamber defined therein, at least one oxygen concentration detecting element formed by an oxygen-pumping element and a cell element, each of the oxygen-pumping element and the cell element being composed of a corresponding one of the walls, and a pair of electrodes with the corresponding wall interposed therebetween, one of the electrodes of the oxygen-pumping element and one of the electrodes of the cell element being arranged within the gas diffusion chamber and being connected to each other, voltage applying means for applying to the oxygen-pumping element a voltage corresponding to a difference between a voltage between the electrodes of the cell element and a predetermined reference voltage to cause pumping current to flow between the electrodes of the oxygen-pumping element, and output detecting means for converting the pumping current into a signal indicative of oxygen concentration, and outputting same.

The oxygen concentration detecting device of the fourth aspect of the invention is characterized by an improvement wherein the one of the electrodes of the oxygen-pumping element and the one of the electrodes of the cell element are connected to each other within the gas diffusion chamber.

Alternatively, the one of the electrodes of the oxygen-pumping element and the one of the electrodes of the cell element may be connected to each other within the basic body at a location other than the gas diffusion chamber and the oxygen concentration detecting element.

BRIEF DESCRIPTION OF THE DRAWINGS

FIG. 2 comprises FIGS. 2A and 2B, constituting in combination is a schematic diagram showing the entire arrangement of a fuel supply control system employing the oxygen concentration detecting device according to first embodiment of the invention;

DETAILED DESCRIPTION

Figure 1:
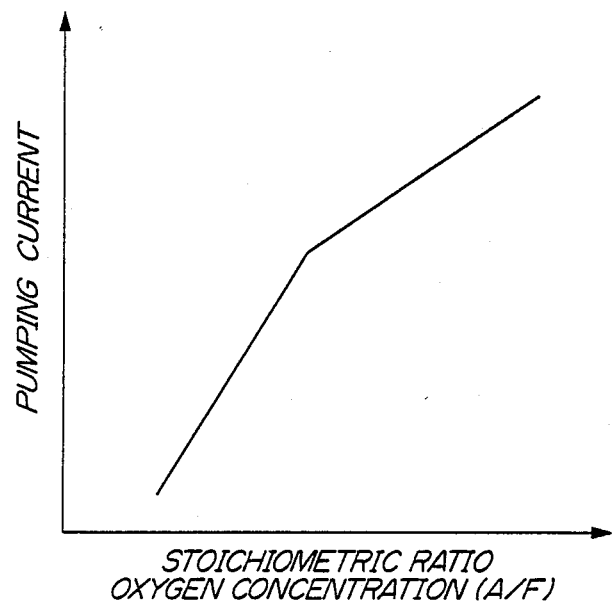
FIG. 1 is a graph showing the detecting characteristic of an oxygen concentration detecting device of the proportional-output type.

The invention will now be described in detail with reference to the drawings showing embodiments thereof.

FIGS. 2–6 show a first embodiment of the invention.

Referring first to FIG. 2, there is illustrated the entire arrangement of a fuel supply control system of an internal combustion engine including an oxygen concentration detecting device according to the first embodiment. Reference numeral 100 designates a body (sensor element section) of the oxygen concentration detecting device (hereinafter called "the O₂ sensor") 1. The sensor body 100 is arranged within an exhaust system of an engine (not shown), in which a three-way catalyst is arranged for purifying ingredients HC, CO, and NOx contained in the exhaust gases emitted from the engine.

Figure 3:
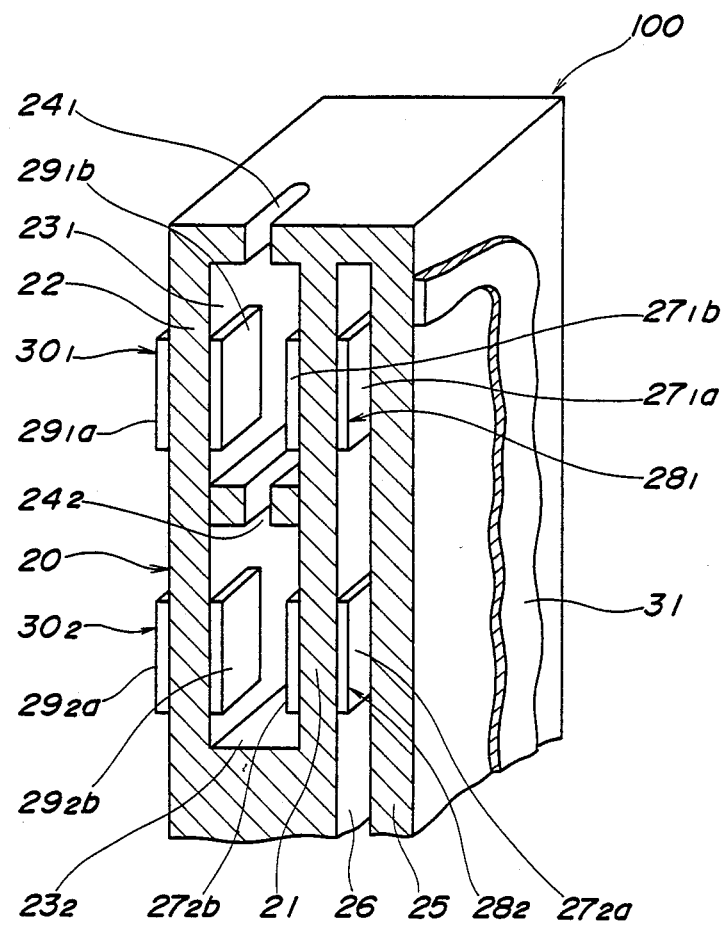
FIG. 3 is a perspective view of the sensor body of the oxygen concentration detecting device in FIG. 2.

As shown in detail in FIG. 3, the sensor body 100 is in the form of a rectangular parallelepiped, and comprises a basic body 20 formed of a solid electrolytic material having oxygen ion-conductivity (e.g. zirconium dioxide ($ZrO_2$)).

The sensor body 100 shown in FIG. 3 is a type which has two oxygen concentration detecting elements longitudinally arranged, each having a cell element and an oxygen pumping element. The basic body 20 of the sensor body 100 has first and second walls 21, 22 extending parallel with each other, between which first and second gas diffusion chamber $23_1$, $23_2$ serving as gas diffusion-limiting zones are defined.

The first gas diffusion chamber $23_1$ is communicated with an exhaust pipe, not shown, of the engine through a first slit $24_1$ which is disposed such that exhaust gases in the exhaust pipe can be guided into the first gas diffusion chamber $23_1$ through the slit $24_1$. The exhaust gases within the first gas diffusion chamber $23_1$ is introduced into the second gas diffusion chamber $23_2$ through a second slit $24_2$ communicating between the two chambers $23_1$ and $23_2$. An air reference chamber 26 to be supplied with air or reference gas is defined between the first wall 21 and an outer wall 25 disposed adjacent the first wall 21 and extending parallel therewith.

In order to detect oxygen concentration within the first gas diffusion chamber $23_1$, a couple of electrodes (first electrodes) $27_1a$, $27_1b$ formed of platinum (Pt) are mounted on opposite side surfaces of the first wall 21, which cooperate with the first wall 21 to form a cell element (sensing cell) $28_1$ for the first oxygen concentration detecting element, while another couple of electrodes $29_1a$, $29_1b$ are similarly mounted on opposite side surfaces of the second wall 22, which cooperate with the second wall 22 to form an oxygen-pumping element (pumping cell) $30_1$ for the first oxygen concentration detecting element.

On the other hand, in order to detect oxygen concentration within the second gas diffusion chamber $23_2$, a cell element $28_2$ for the second oxygen concentration detecting element having a couple of electrodes $27_2a$, $27_2b$, and an oxygen-pumping element $30_2$ for the second oxygen concentration detecting element having a couple of electrodes $29_2a$, $29_2b$, are respectively mounted on the first and second walls 21, 22, similarly to the cell element $28_1$ and the oxygen-pumping element $30_1$.

A heater (heating element) 31 is provided on an outer side surface of the outer wall 25, for heating the cell elements $28_1$, $28_2$ and the oxygen-pumping elements $30_1$, $30_2$ to activate them.

As shown in FIG. 2, the electrodes $27_1b$ and $29_1b$ for the first oxygen concentration detecting element, which are located on the first gas diffusion chamber $23_1$ side, are connected with each other (in the embodiment of FIG. 2, they are connected by a suitable electrically conductive member $32_1$), and are connected to an inverting input terminal of an operational amplifier 41 through a line 1.

On the other hand, the other electrode $27_1a$ of the cell element $28_1$ for the first oxygen concentration detecting element is connected to an inverting input terminal of a differential amplifier circuit $42_1$ for the first oxygen concentration detecting element. The differential amplifier circuit $42_1$ forms a voltage-applying circuit together with a reference voltage source $43_1$ connected to an non-inverting input terminal thereof for applying to the oxygen-pumping element $30_1$ a voltage corresponding to the difference between a voltage (cell element voltage) developed between the electrodes $27_1a$ and $27_1b$ of the cell element $28_1$ (in the FIG. 2 embodiment, the sum of a voltage on the line 1 and the cell element voltage) and a reference voltage $V_{so}$ from the reference voltage source $43_1$.

In the present embodiment, the reference voltage $V_{so}$ of the reference voltage source $43_1$ is set to a value of the sum of the cell element voltage developed across the cell element $28_1$ when the air-fuel ratio of a mixture supplied to the engine is equal to a stoichiometric mixture ratio, e.g., 0.45 volts and a predetermined reference voltage, hereinafter referred to, applied to a non-inverting input terminal, of the operational amplifier 41.

The differential amplifier circuit $42_1$ has an output thereof connected to the electrode $29_1a$ of the oxygen-pumping element $30_1$ remote from the first gas diffusion chamber $23_1$ by way of a switch $44_1$ of a switching circuit 44. The switching circuit 44 is controlled to close or open in dependence on activation and non-activation of the sensor body 100 as well as on operating conditions of the engine. More specifically, when the sensor body 100 is inactivated, both of the switches $44_1$ and $44_2$ are opened, and on the other hand, when it is activated, one of the switches is closed in response to operating conditions of the engine.

The non-inverting input terminal of the operational amplifier circuit 41 is connected to a reference voltage source 45 to be supplied with the predetermined reference voltage therefrom. A current detecting resistance 46 for detecting pumping current Ip is connected between an output terminal of the operational amplifier circuit 41 and the line 1 or an inverting input terminal of the operational amplifier circuit 41. That is, the resistance 46 also serves as the negative feedback resistance of the operational amplifier circuit 41.

In the operational amplifier 41 connected as above, provided that there is no offset in the output of the circuit 41, when the air-fuel ratio is equal to the stoichiometric ratio, no pumping current Ip flows in the line 1 and applied to the inverting input terminal of the circuit 41 according to the input level setting for the differential amplifier $42_1$, and then the output voltage is equal to the reference potential at the non-inverting input terminal, and an electric potential at the inverting input terminal is also equal to the reference potential. On the other hand, when the air-fuel ratio is not equal to the stoichiometric ratio, pumping current is supplied to the inverting input terminal, an output voltage is generated at the output of the circuit 41, which corresponds to the amplification degree or factor (even if it is 1) determined by the value of the resistance 46. Although the output voltage varies in response to the magnitude of the pumping current Ip, the potential at the inverting input terminal is maintained at a constant value substantially equal to the reference potential at the non-inverting input terminal due to the action of the operational amplifier 41.

More specifically, in the above described construction, when no pumping current Ip flows in the line 1, i.e., Ip is zero, the output voltage $I_{PVW}$ of the operational amplifier 41 (i.e., the voltage at one end of the resistance 46) is made equal to the reference voltage $V_{REF}$ from the reference voltage source 45, and at the same time a voltage $V_{CENT}$ applied to the inverting input terminal (i.e., the voltage in the line 1 and at the other end of the resistance 46) is made equal to the reference voltage $V_{REF}$.

Further, even when the pumping current Ip is not zero and varies within the lean side or within the rich side in response to the air-fuel ratio of the supplied mixture, as hereinafter referred to, the voltage at the inverting input terminal of the operational amplifier 41 or at the other end of the resistance 46 connected to the line 1, is made substantially equal to the voltage at the non-inverting input terminal, i.e., the reference voltage $V_{REF}$, irrespective of a change in the pumping current Ip.

As described above, the voltage $V_{CENT}$ in the line 1 and accordingly at the other end of the resistance 46 is maintained substantially at the voltage $V_{REF}$, irrespective of whether the pumping current Ip assumes zero or varies. On the other hand, the voltage at the one end of the resistance 46 connected to the output of the operational amplifier circuit 41 is varied in response to the direction of the pumping current Ip (the positive direction or the negative direction) and the amount of the current Ip. Therefore, the voltage $V_{CENT}$ is a reference value (reference voltage) for detecting current flowing through the oxygen-pumping element and calculating the air-fuel ratio based on the detected current value.

In this sense, the potential on the line 1 is not the earth potential, but the whole system including the line 1 and the current detecting resistance 46 is raised in potential from the ground level by the reference voltage $V_{REF}$. Consequently, when the pumping current Ip is determined from a potential difference between the opposite ends of the current detecting resistance 46, that is, from the respective voltages $V_{CENT}$ and $I_{PVW}$, as hereinafter described, the reference value $V_{CENT}$ as well as the other end voltage $I_{PVW}$ are always positive voltages, irrespective of whether the pumping current Ip flows in the positive direction or in the negative direction in response to the air-fuel ratio, thereby facilitating the calculation of the air-fuel ratio.

Further, the pulling-up of the reference voltage of the pumping current detecting system to the constant reference voltage as above is advantageous for avoiding erroneous detection of the current due to noise, especially high level noise such as ignition pulse noise of the engine.

The voltage $V_{REF}$ of the reference voltage source 45 of the operational amplifier circuit 41 is set to a predetermined voltage (e.g., 2.5 volts) also for ensuring the above described advantage.

The second oxygen concentration detecting element of the sensor body 100 has a construction similar to the first oxygen concentration detecting element. That is, in the voltage applying circuit and the switching circuit 44, there are respectively provided a differential amplifier circuit $42_2$, a reference voltage source $43_2$, and the aforementioned switch $44_2$. The switch $44_2$ is connected to the other side electrode $29_2a$ of the oxygen-pumping element $30_2$, and the respective inner side electrodes $27_2b$ and $29_2b$ of the cell element $28_2$ and the oxygen-pumping element $30_2$ are both connected to the line 1, so that, during the use of the second oxygen concentration detecting element, the pumping current Ip flowing through the oxygen-pumping element $30_2$ flows in the line 1.

The output voltage $I_{PVW}$ of the operational amplifier circuit 41 and the voltage $V_{CENT}$ on the line 1, at the opposite ends of the current detecting resistance 46, are supplied to an input port 401 of an electronic control unit (hereinafter called "the ECU") 4, and are at the same time supplied to respective inputs of a differential amplifier circuit 47.

The differential amplifier circuit 47 amplifies the difference between the voltage $V_{CENT}$ and the output voltage $I_{PVW}$ of the operational amplifier circuit 41, and thus serves to improve the accuracy of a signal indicative of a voltage detected from pumping current Ip which assumes 0 or a value close thereto, i.e., where the air-fuel ratio is within a predetermined range about the stoichiometric air-fuel ratio of the mixture. In the differential amplifier circuit 47, the $I_{PVW}$ signal is amplified by a predetermined magnification α, e.g., 5 times, to be produced as a voltage $I_{PVN}$.

The output voltage $I_{PVN}$ of the differential amplifier circuit 47 is obtained by the following equation, and is also supplied to the input port 401:

$$I_{PVN} = -5(I_{PVW} - V_{CENT}) + V_{CENT} \quad (1)$$

Therefore, three voltage signals, i.e., $V_{CENT}$ as the reference voltage, $I_{PVW}$, and $I_{PVN}$ are supplied to the input port 401 for calculating the air-fuel ratio based on the pumping current Ip. Although the pumping current can be detected by using only the voltages $V_{CENT}$ and $I_{PVW}$ (a first manner of calculating the pumping current Ip), it can be more accurately detected by additional using the voltage $I_{PVN}$ (a second manner of calculating the pumping current Ip) when the air-fuel ratio is in the vicinity of the stoichiometric air-fuel ratio of the mixture in which the pumping current Ip assumes small values.

Figure 4:
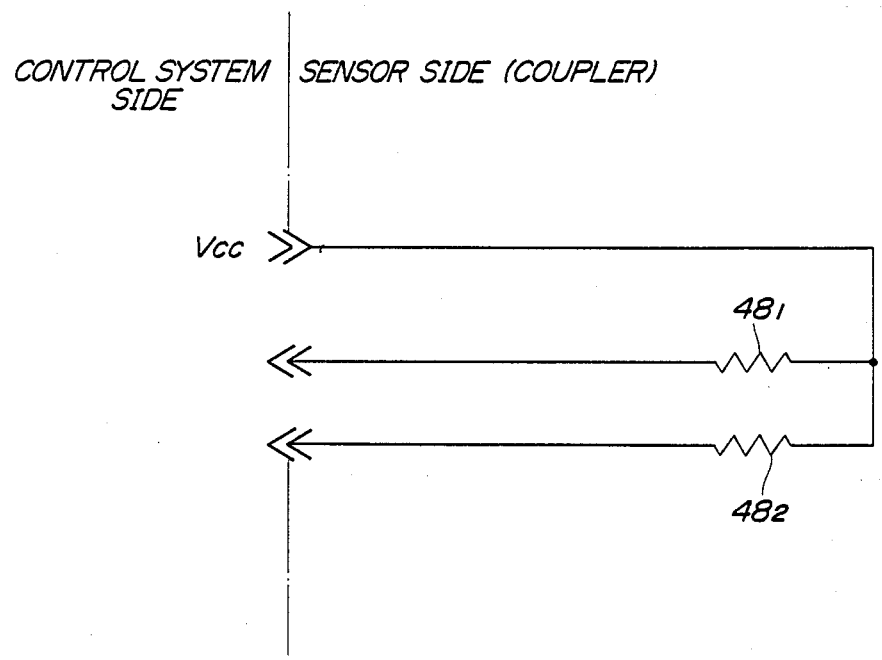
FIG. 4 is a schematic diagram showing connection of label correction resistances to a control system for the device in FIG. 2.

Also supplied to the input port 401 is variation correcting value information for correcting variations in the detected air-fuel ratio due to variations between sensor bodies used. This information may be supplied individually for each of the first and second oxygen concentration detecting elements, if the sensor body 100 has two oxygen detecting elements as in the illustrated embodiment of the invention. Specifically, the information may be supplied by utilizing label correction resistances $48_1$ and $48_2$, as shown in FIG. 4.

The values of the label correction resistances $48_1$ and $48_2$ are set to values corresponding to variations in the characteristics of sensor bodies compared with a standard sensor body. The degree of variation in the characteristics of individual sensor body is indicated by a label indicative of its resistance value. The label correction resistances $48_1$ and $48_2$ are used together with the sensor body 100 used. That is, for instance, they may be provided within a connection coupler (not shown) arranged in a wire harness (not shown), connecting the sensor body 100 to the ECU 4, hereinafter referred to. When the sensor body 100 is electrically connected to the ECU 4, respective one ends of the resistances $48_1$, $48_2$ are connected to a predetermined voltage source Vcc, as shown in FIG. 4, whereby the variation correcting value information corresponding to their resistance values is inputted through the other ends of the resistances.

The input port 401 of the ECU 4 is provided therein with an A/D (analog-to-digital) converter, which converts the above-mentioned input analog signals to digital signals.

The ECU 4 is supplied with respective output signals from a throttle valve opening (θth) sensor 10, and an intake pipe absolute pressure (PBA) sensor 12 an engine parameter sensors, which then have their voltage levels shifted to a predetermined level by a level shifter circuit 402 and successively applied to the A/D converter 404 through a multiplexer 403. The A/D converter 404 of the input port 401 supplies the digitally-converted data to a central processing unit (hereinafter called "the CPU") 406 via a data bus 405.

An output signal from an engine speed (Ne) sensor 14 is applied to a waveform shaper circuit 407 to have its pulse waveform shaped, and the shaped signal is supplied to the CPU 406 as a top-dead center position (TDC) signal, as well as to a counter 408. The counter 408 counts the time interval between an immediately preceding pulse of the TDC signal and a present pulse of same, inputted thereto from the Ne sensor 14. The counted value Me is proportional to the reciprocal of the actual engine rotational speed Ne. The counter 408 supplies the counted value Me to the CPU 406 via the data bus 405.

Further connected to the CPU 406 via the data bus 405 are a read-only memory (hereinafter called "the ROM") 409, and a random access memory (hereinafter called "the RAM") 410, and driving circuits 412–414. The RAM 410 temporarily stores results of calculations executed within the CPU 406, while the ROM stores a control program to be executed within the CPU 406 for calculation of a fuel injection period $T_{OUT}$ of fuel injection valves 11, and other various programs, as well as various maps and tables.

The CPU 406 determines whether to energize or deenergize the heater 31 and whether to close or open the switches $44_1$ and $44_2$, and then supplies driving signals corresponding to the determinations to the heater 31 and the switching circuit 44 via the driving circuits 412 and 413.

The CPU 406 determines operating conditions of the engine such as a feedback control condition, based on the aforementioned various engine parameter signals including an output signal from the $O_2$ sensor 1, and calculates the fuel injection period of the fuel injection valves 11 in synchronism with the TDC signals in response to the determined engine operating conditions, based on a control program (not shown), by the use of the following equation (2):

$$T_{OUT} = T_i \times K_{O2} \times K_1 + K_2 \qquad (2)$$

where $T_i$ represents a basic fuel injection period, which is calculated from a Ti map (not shown), stored in the ROM 409, in response, e.g., to the absolute pressure PBA within the engine intake pipe, and the engine rotational speed Ne. $K_{O2}$ represents an air-fuel ratio correction coefficient, which is determined, in response to oxygen concentration in the actual exhaust gases, based on a control program (not shown), when the engine is in the feedback control region, while it is set to a predetermined value when the engine is in an open loop control region. $K_1$ and $K_2$ respectively represent other correction coefficients and correction variables obtained in response to various engine parameter signals, and are set to such desired values as to be able to optimize operating characteristics of the engine, such as fuel consumption and accelerability.

The CPU 406 supplies the driving signals responsive to the results of the above calculation to the fuel injection valves 11 via the driving circuit 414. The air-fuel ratio is thus feedback-controlled to a desired ratio or stoichiometric ratio during the feedback operating condition of the engine.

The oxygen concentration is detected by the $O_2$ sensor in the following manner.

First, when the first oxygen concentration detecting element is selected, as shown in FIG. 2, the exhaust gases are introduced into the first gas diffusion chamber $23_1$ through the first slit $24_1$ with operation of the engine. This causes a difference in oxygen concentration between the first gas diffusion chamber $23_1$ and the air reference chamber 26 into which air is introduced. Consequently, a voltage (sensor voltage) corresponding to the difference is developed between the electrodes $27_{1a}$ and $27_{1b}$ of the cell element $28_1$, which is added to the line 1 voltage $V_{CENT}$, and the same is applied to the inverting input terminal of the differential amplifier circuit $42_1$. As stated before, the reference voltage $V_{so}$ supplied to the non-inverting input terminal of the differential amplifier circuit $42_1$ is set to the sum of a voltage developed across the cell element $28_1$ when the air-fuel ratio is equal to the stoichiometric air-fuel ratio, and the reference voltage $V_{REF}$ supplied to the operational amplifier circuit 41.

Therefore, when the air-fuel ratio is on the lean side, the voltage between the electrodes $27_{1a}$ and $27_{1b}$ of the cell element $28_1$ is lowered, while the line 1 voltage $V_{CENT}$ is maintained at $V_{REF}$, so that the sum of the voltage between the electrodes $27_{1a}$ and $27_{1b}$ and the $V_{CENT}$ becomes lower than the reference voltage $V_{so}$. Thus, the output level of the differential amplifier circuit $42_1$ becomes positive, and the positive level voltage is applied to the oxygen-pumping element $30_1$ via the switch $44_1$. By applying the positive level voltage, when the oxygen-pumping element $30_1$ is activated, oxygen present within the gas diffusion chamber $23_1$ is ionized, whereby the resulting ions move through the electrode $29_{1b}$, the second wall 22, and electrode $29_{1a}$, to be emitted therefrom as oxygen gas or pumped out of the $O_2$ sensor 1. That is, the direction of flow of the pumping current Ip from the electrode $29_{1a}$ to the electrode $29_{1b}$ flows through the current detecting resistance 46 via the line 1. At this time, the pumping current Ip flows from the line 1 to the output side of the operational amplifier circuit 41.

On the other hand, when the air-fuel ratio is on the rich side, the sum of the voltage between the electrodes $27_{1a}$ and $27_{1b}$ of the cell element $28_1$ and the line 1 voltage $V_{CENT}$ becomes higher than the reference voltage $V_{so}$, so that the output level of the differential amplifier circuit $42_1$ becomes negative. Consequently, reversely to the above described action, external oxygen is pumped into the gas diffusion chamber $23_1$ through the oxygen-pumping element $30_1$, and simultaneously the pumping current Ip flows from the electrode $29_{1b}$ to the electrode $29_{1a}$ and flows through the current detecting resistance 46, that is, the direction of flow of the pumping current Ip is reversed to the above case.

When the air-fuel ratio is equal to the stoichiometric air-fuel ratio, the sum of the voltage between the electrodes $27_{1a}$ and $27_{1b}$ of the cell element $28_1$ and the line 1 voltage $V_{CENT}$ becomes equal to the reference voltage $V_{so}$, so that the pumping-in and out of oxygen is not effected, whereby no pumping current flows (that is, the pumping current Ip is zero).

As described above, since the pumping-in and out of oxygen and hence the pumping current Ip are controlled so as to maintain the oxygen concentration in the gas diffusion chamber $23_1$ at a constant level, the pumping current Ip assumes a value proportional to the oxygen concentration of the exhaust gases on both the lean side and rich side of the air-fuel ratio of the supplied mixture.

Signals for detecting the amount of the pumping current Ip flowing through the current detecting resistance 46, e.g., signals indicative of respective voltages $I_{PVW}$, $V_{CENT}$, $I_{PVN}$ at the opposite ends of the resistance 46 are supplied to the ECU 4.

Similarly to the first oxygen concentration detecting element, when the second oxygen concentration detecting element is used (that is, when the switch $44_2$ of the switching circuit 44 is closed (reversely to the position shown in FIG. 2), the pumping-in and out of oxygen is controlled so as to maintain the oxygen concentration in the second gas diffusion chamber $23_2$ at a constant value, that is, the voltage between the electrodes $27_{2a}$ and $27_{2b}$ of the cell element $28_2$ is feedback-controlled to be maintained at a constant value, and at the same time the signals indicative of the voltage $I_{PVW}$, $V_{CENT}$, $I_{PVN}$ for detecting the pumping current Ip flowing during the feedback control are supplied to the ECU 4 as outputs of the second oxygen concentration detecting element.

According to the aforementioned first manner of calculating the pumping current Ip, the ECU 4 calculates the pumping current Ip based on the voltages $I_{PVW}$ and $V_{CENT}$. More specifically, the voltages $I_{PVW}$ and $V_{CENT}$ converted to digital signals by the A/D converter in the input port 401 of the ECU 4 are substituted into the following equation (3) to determine the pumping current Ip:

$$Ip = (I_{PVW} - V_{CENT})/Rp \quad (3)$$

where Rp represents the resistance value of the resistance 46. That is, since the pumping current Ip flows through the resistance 46, the pumping current Ip can be obtained by dividing the voltage across the resistance 46, i.e., $(I_{PVW} - V_{CENT})$ by the resistance value Rp. Then, the ECU 4 reads out an air-fuel ratio corresponding to the calculated pumping current Ip from a data map stored in the ROM 409 to detect the present air-fuel ratio, and thereafter determines the correction coefficient $K_{02}$ in accordance with the difference between the detected air-fuel ratio and a desired ratio or stoichiometric ratio, thereby adjusting the amount of secondary air or fuel to be supplied to the engine. In this way, the basic feedback-control of the air-fuel ratio is carried out. When the detected air-fuel ratio is equal to the stoichiometric ratio, the voltage $I_{PVW}$ becomes equal to the voltage $V_{CENT}$ and hence the pumping current becomes zero. Since the voltage $I_{PVW}$ becomes substantially equal to the reference voltage $V_{REF}$ of the reference voltage source 45, even if there is any output error in the source 45, the voltage $I_{PVW}$ is equal to the voltage $V_{CENT}$ when no pumping current Ip flows, so that the pumping current Ip becomes zero from the equation (3) when the air-fuel ratio is equal to the stoichiometric ratio.

Figure 5:
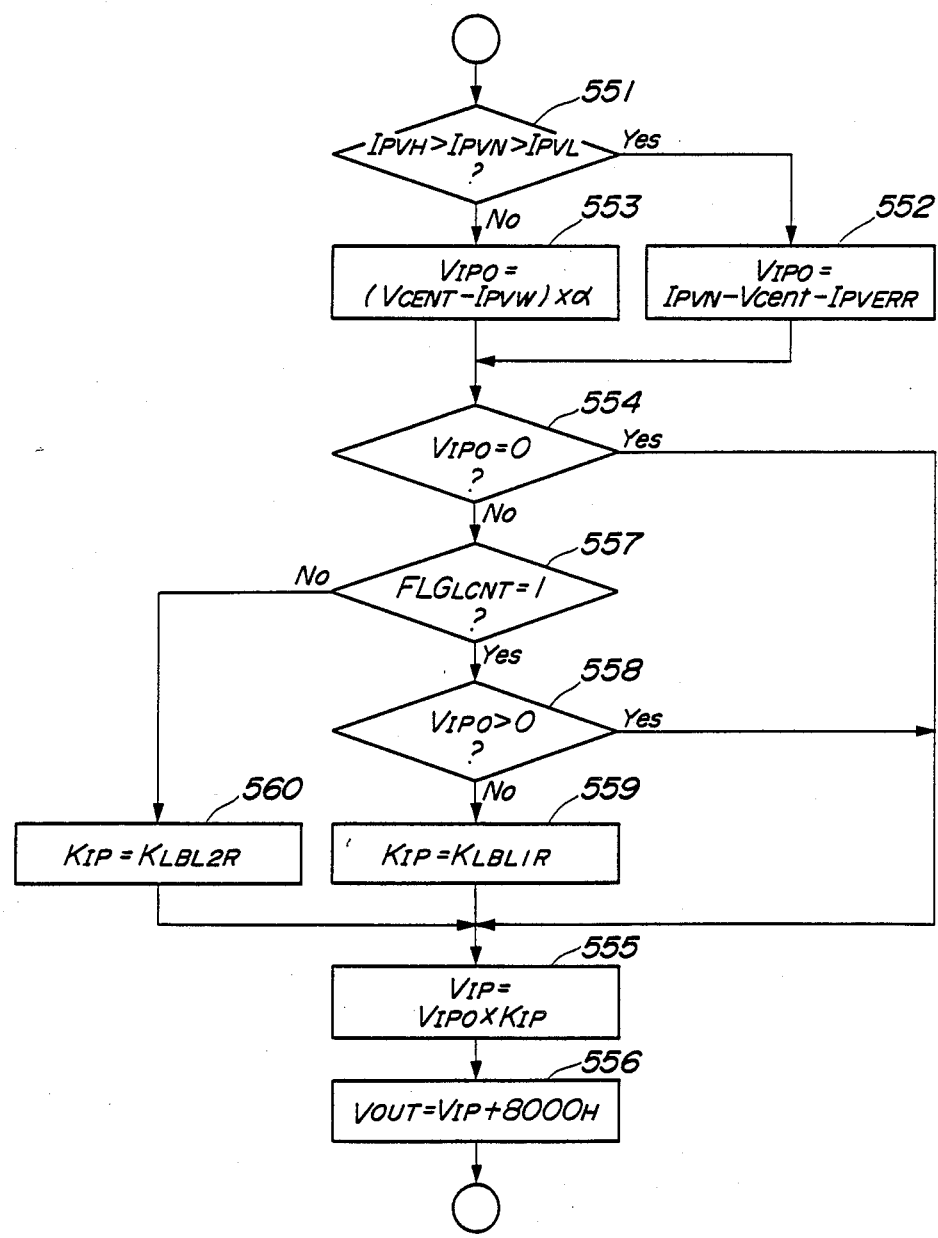
FIG. 5 is a subroutine for calculating a voltage value corresponding to a pumping current of the oxygen concentration detecting device in FIG. 2.

FIG. 5 shows another manner of calculating the pumping current Ip to calculate the air-fuel ratio (the second manner). This manner includes correction of the sensor output so as to calculate the air-fuel ratio in a more precise manner. This program is executed in the CPU 406 in synchronism with TDC signal pulses. According to the calculation manner of FIG. 5, the pumping current Ip is calculated in terms of a voltage $I_{OUT}$, in response to which the air-fuel ratio feedback correction coefficient $K_{02}$ is determined.

At a step 551, it is determined whether or not the output voltage $I_{PVN}$ of the differential amplifier circuit 47 is within a predetermined small value range with a middle value about which the voltage $I_{PVN}$ varies. That is, it is determined whether or not the $I_{PVN}$ is larger than a first predetermined value $I_{PVL}$ (e.g. 2.3 volts) and at the same time smaller than a second predetermined value $I_{PVH}$ (e.g. 2.6 volt). Depending upon the answer to the question of the step 551, it is determined whether to determine a voltage $V_{IPO}$ corresponding to the pumping current Ip either by using the voltage $I_{PVW}$ which is a direct output of the operational amplifier circuit 41, or by using the voltage $I_{PVN}$ which is obtained by amplifying the $I_{PVW}$ voltage by the differential amplifier circuit 47.

If the answer to the question of the step 551 is Yes, that is, if the voltage $I_{PVN}$ fulfills the condition $I_{PVH} > I_{PVN} > I_{PVL}$ (which means that the pumping current Ip assumes a small value equal to 0 or in the vicinity of 0, and that the air-fuel ratio is within a narrow range about the stoichiometric air-fuel ratio (e.g., 14.7)), the value $I_{VPO}$ is calculated by the following equation (step 552):

$$V_{IPO} = I_{PVN} - V_{cent} - I_{PVERR} \quad (4)$$

where $V_{cent}$ represents a reference voltage for the voltage $V_{CENT}$ at the end of the current detecting resistance 46 remote from the output of the operational amplifier circuit 41, while $I_{PVERR}$ represents a correction value for compensating for circuit errors such as the offset of the operational amplifier circuit 41.

The calculation at the step 552 is based on the following ground:

By using the voltage $I_{PVN}$ which is obtained by amplifying the voltage $I_{PVW}$ by the operational amplifier circuit 47 when the voltage $I_{PVN}$ assumes a value within the small value range of the step 552, it is possible to enhance the accuracy of calculation of the pumping current Ip. If the air-fuel ratio is changed to the lean side or to the rich side from the above small value range where the air-fuel ratio is equal to or close to the stoichiometric air-fuel ratio (14.7), such change exerts a great influence upon the purification degree i.e. conversion efficiency of the three-way catalyst. Therefore, more accuracy is required in detecting the air-fuel ratio than when the air-fuel ratio is changed within a range remote from the stoichiometric air-fuel ratio. In order to improve the detection accuracy in an air-fuel ratio range in the vicinity of the stoichiometric air-fuel ratio, the direct output voltage $I_{PVW}$ is not directly used but the amplified voltage $I_{PVN}$ is applied to calculation of the voltage value $V_{IPO}$, which is obtained by amplifying $I_{PVW}$ by a predetermined number of times $a$.

In the equation (4), the subtraction of the reference voltage $V_{cent}$ is effected for correcting the reference potential or zero potential.

As stated before, the potential of the pumping current detecting system, including the current detecting resistance 46 and the operational amplifier circuit 41, is pulled up by the reference voltage $V_{REF}$ to always maintain the voltages at the opposite ends of the resistance 46 at a positive level even if the direction of flow of the pumping current Ip is changed. Therefore, the voltage at the end of the resistance 46 close to the output of the operational amplifier circuit 41 varies about the reference voltage $V_{REF}$ from the reference voltage source 45, in response to the direction of flow of the pumping current Ip and the amount of the same current. Thus, the amount of the pumping current Ip can be determined from the difference between the reference voltage $V_{REF}$ and a voltage varying in response to the flow of the pumping current Ip. Therefore, at the step 552 the reference voltage $V_{cent}$ is subtracted.

The reference voltage $V_{cent}$ corresponds to the line 1 voltage $V_{CENT}$. If there is no circuit error in the operational amplifier circuit 41, etc., and the pumping current Ip is zero (that is, the air-fuel ratio is equal to the stoichiometric air-fuel ratio), the value $V_{cent}$ should be set to a value equal to the reference voltage $V_{REF}$.

Therefore, by obtaining $(I_{PVN} - V_{cent})$, even of there is an error (e.g. setting error) in the voltage from the reference voltage source 45, or even if the voltage from the source 45 varies, the value $(I_{PVN} - V_{cent})$ is always zero when the actual pumping current Ip is zero. This correction enables detecting the pumping current accurately. Thus, the air-fuel ratio detection accuracy is improved especially when the air-fuel ratio is in the vicinity of the stoichiometric air-fuel ratio (14.7), in addition to the aforementioned advantage of being noise proof.

Referring again to the step 552, the correction value $I_{PVERR}$ is subtracted from $(I_{PVN} - V_{cent})$, whereby the detection accuracy can be further enhanced.

Although, in the above explanation, it has been assumed that there is no circuit error such as the offset in the operational amplifier circuit 41, actually there can be such an error in the circuit 41.

The offset voltage of an operational amplifier used as an amplifier is different between individual operational amplifiers and also varies due to aging change.

If there exists an offset voltage in the operational amplifier, then even when the air-fuel ratio actually remains unchanged, the detected pumping current Ip can show different values. That is, such error is liable to appear as noise in the pumping current Ip, which prevents accurate detection of the air-fuel ratio. Especially, in the vicinity of the stoichiometric air-fuel ratio, where the pumping current Ip assumes a small value near 0, the difference between the reference voltage $V_{cent}$ and the output voltage $I_{PVN}$ is small, so that the above described circuit error can exert a great influence upon the detection result.

In order to correct the circuit error, the subtraction of the correction value $I_{PVERR}$ is executed at the step 552. The correction value $I_{PVERR}$ corresponds to the difference between voltages appearing at the output and input of the differential amplifier 47 when no pumping current Ip is applied to the input of the amplifier 47. The value $I_{PVEPR}$ is previously determined and stored in the RAM 410, before detection of the air-fuel ratio, during a state where no pumping current is supplied to the current detecting resistance 46.

Figure 6:
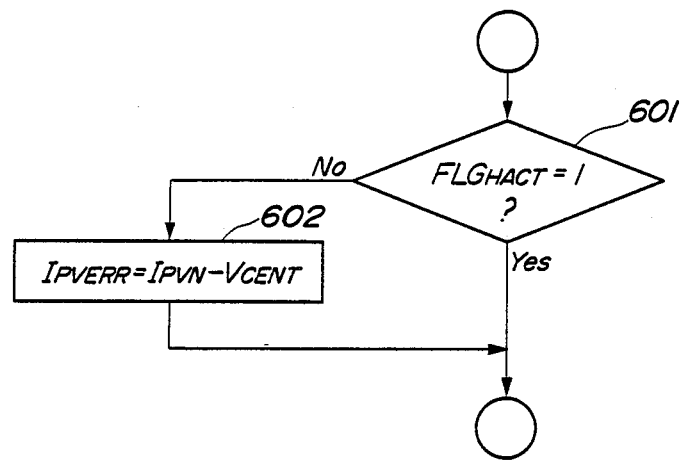
FIG. 6 is a flow chart showing a subroutine for calculating an IPVERR value corresponding to a circuit error of an amplifier included in the oxygen concentration detecting device in FIG. 2.

FIG. 6 shows a flowchart of a subroutine for calculating the correction value $I_{PVERR}$ applied at the step 552 for correcting the circuit error of the operational amplifier circuit.

At a step 601 it is determined whether or not a flag $FLG_{HACT}$ has been set to a value of 1. The flag $FLG_{HACT}$ indicates whether or not the heater 31 has been activated. When it is set to 1, it indicates that the heater 31 is in a completely activated state, while when it is set to 0, it indicates that the heater is in an inactivated state.

If the answer to the question of the step 601 is No, that is, if the flag $FLG_{HACT}$ has been set to 0, it is assumed that the condition for calculating the correction value $I_{PVERR}$ is fulfilled, and the program proceeds to a step 602, where the correction value $I_{PVERR}$ is calculated and the resulting $I_{PVERR}$ value is stored into the RAM 410, followed by termination of the program.

Before the heater 31 becomes activated, both the switches $44_1$ and $44_2$ of the voltage applying circuit 44 are kept open. Consequently, on such an occasion the supply of the pumping current Ip is stopped (Ip is zero), so that the correction value $I_{PVERR}$ can be determined.

The $I_{PVERR}$ value is specifically calculated by subtracting the line 1 voltage $V_{CENT}$ from the output voltage $I_{PVN}$ value of the differential amplifier circuit 47. Since the $I_{PVN}$ value contains a voltage component corresponding to the circuit error, if it exists, the circuit error amount is accurately obtained by calculating the difference ($I_{PVN} - V_{CENT}$) between $I_{PVN}$ and $V_{CENT}$ which is kept constant. The resulting value ($I_{PVN} - V_{CENT}$) is stored as the offset amount of the amplifier to be applied for correcting the actual amplifier output after completion of the activation of the heater 31.

On the other hand, if the answer to the question of the step 601 is Yes, that is, if the flag $FLG_{HACT}$ is set to 1, it is assumed that the activation of the heater 31 has been completed and therefore oxygen concentration can now be detected by the $O_2$ sensor 1 on the basis of the pumping current Ip. Then, the calculation of the $I_{PVERR}$ value is interrupted, and the program is terminated. In this way, an up-to-date value of the $I_{PVERR}$ calculated immediately before the completion of activation of the heater 31 is stored in the RAM 410, thereby enabling to properly correct the voltage $V_{IPO}$.

Referring again to FIG. 5, at the step 552, the correction value $I_{PVERR}$ is read from the RAM 410 and is subtracted from ($I_{PVN} - V_{cent}$), to thereby remove the circuit error contained in the present value ($I_{PVN} - V_{cent}$), whereby the voltage value $V_{IPO}$ accurately corresponds to the actual pumping current Ip.

If the answer to the question of the step 551 is No, that is, if $I_{PVN} \geq I_{PVH}$ or $I_{PVN} \leq I_{PVL}$ is fulfilled, which means the value of $I_{PVN}$ is out of the predetermined range, it is assumed that the pumping current Ip has neither a value of 0 nor a small value in the vicinity of 0, that is, the air-fuel ratio is not in the vicinity of the stoichiometric air-fuel ratio (14.7). The program then proceeds to a step 553, in which the value $V_{IPO}$ is calculated by the following equation:

$$V_{IPO} = (V_{CENT} - I_{PVW}) \times a \qquad (5)$$

where $a$ is a predetermined value. That is, when the air-fuel ratio is not in the vicinity of the stoichiometric air-fuel ratio, the voltage $I_{PVW}$ value is directly used as the terminal voltage of the current detecting resistance 46 close to the output of the operational amplifier circuit 41, and the voltage $V_{IPO}$ is obtained by calculating the difference between the line 1 voltage $V_{CENT}$ as the other terminal voltage of the resistance 46 and $I_{PVW}$, that is, ($V_{CENT} - I_{PVW}$). Therefore, in order to raise up the resulting value of $V_{IPO}$ to the same level as that of the resulting value obtained at the step 552, the difference ($V_{CENT} - I_{PVW}$) is multiplied by the predetermined value.

Also in the calculation at the step 553, the voltage $V_{IPO}$ value is obtained by using the pulled-up voltage $V_{CENT}$ in the line 1 and on the basis of the difference ($V_{CENT} - I_{PVW}$), so that a potential correction is effected similarly to the step 552, whereby the voltage $V_{IPO}$ corresponding to the pumping current Ip is accurately detected irrespective of the influence of noise and error in the reference voltage $V_{REF}$.

At a step 554, it is determined whether or not the $V_{IPO}$ value obtained at the step 552 or 553 is equal to 0, in order to judge whether or not the present air-fuel ratio is equal to the stoichiometric ratio. If the answer is Yes, that is, if Ip is equal to zero, the program jumps to a step 555 to execute the step 555 and a step 556, followed by termination of the program.

At the step 555, the $V_{IPO}$ value obtained at the step 552 or 553 is corrected to a $V_{IP}$ value by being multiplied by a label resistance coefficient $K_{IP}$. Then at the step 556, the value $V_{IP}$ obtained at the step 555 is increased by a predetermined number, e.g. 8000 in hexadecimal notation, to obtain a value $V_{OUT}$ as the output voltage.

At the step 554, if it is determined that the value $V_{IPO}$ is zero, the value $V_{IP}$ obtained at the step 555 is also zero, and therefore, the resulting $V_{OUT}$ value at the step 556 is 8000 in hexadecimal notation. The predetermined number is a reference or middle value of the $V_{OUT}$ value. When the air-fuel ratio is changed from the stoichiometric ratio to the lean side or to the rich side, the $V_{OUT}$ value is calculated by addition or subtraction of the present value of $V_{IP}$ to or from the middle value, in accordance with the $V_{IP}$ value (the $V_{IPO}$ value assumes a positive value when the air-fuel ratio is on the lean side with respect to the stoichiometric ratio, and a negative value when the latter is on the rich side, and the $V_{IP}$ value also assumes a positive value or a negative value correspondingly).

As stated above, the voltage value $V_{IP}$ obtained at the step 555 is not made as the final value, but it is increased by the predetermined number at the step 556. This is for preventing the $V_{OUT}$ value from assuming a value of 0 even when the air-fuel ratio is equal to the stoichiometric ratio where the pumping current Ip is 0, to thereby enable avoiding an inconvenience encountered when the $K_{O2}$ value is determined on the basis of the $V_{OUT}$ value, e.g. when the $K_{O2}$ value is obtained by division.

If the answer to the question of the step 554 is No, it is determined at a step 557 whether or not a flag $FLG_{LCNT}$ has been set to a value of 1. If the answer at the step 557 is Yes, it is determined that the first oxygen concentration detecting element in FIG. 2 is not being used, and then the program proceeds to step 558.

The flag $FLG_{LCNT}$ indicates whether the first oxygen concentration detecting element or the second oxygen concentration detecting element is being used. That is, when the first oxygen concentration detecting element is used, the value N is set to 1, while it is set to 2 when the second oxygen concentration detecting element is being used.

At the step 558, it is determined whether or not the present $V_{IPO}$ value is larger than zero (i.e. positive or negative). That is, it is determined whether the air-fuel ratio is on the lean side or on the rich side with respect to the stoichiometric ratio.

If the answer to the question of the step 558 is Yes, that is, if the $V_{IPO}$ value is positive, it is determined that the air-fuel ratio is on the lean side, and then the program proceeds to the step 555. On the other hand, if the answer is No, that is, if the $V_{IPO}$ value is negative, it is determined that the air-fuel ratio is on the rich side, and then the program proceeds to a step 559, where the $K_{IP}$ value is set to a predetermined value $K_{LBL1R}$, followed by execution of the steps 555 and 556 and then termination of the program.

The predetermined value $K_{LBL1R}$ at the step 555 is a correction coefficient for correcting variations in output characteristic between $O_2$ sensors when the air-fuel ratio is not the stoichiometric air-fuel ratio, in such a manner that the $V_{IPO}$ value is corrected toward a richer value when the pumping current Ip is below zero during use of the first oxygen concentration detecting element.

The correction coefficient $K_{LBL1R}$ is obtained by a subroutine, not shown, wherein it is determined based on the value of the label correction resistance $48_1$ for the first oxygen concentration detecting element.

In the arrangement shown in FIG. 4, a single label correction resistance is used for each detecting element. Even only a single label correction resistance can execute correction on both of the lean and rich sides for the following reason:

Since the air-fuel ratio vs. pumping current characteristic of a proportional-output type $O_2$ sensor in general has correlation in variation between the rich side and the lean side, the actual label correction resistance value may be, for instance, determined on the rich side when the pumping current Ip value is negative, while a correction value on the lean side may be determined by multiplying the determined label correction resistance value on the rich side by a predetermined number of times, or vice versa.

If the answer to the question of the step 557 is No, it is judged that the second oxygen concentration detecting element is now being used, and then the program proceeds to a step 560, where the $K_{IP}$ value is set to a second predetermined value $K_{LBL2R}$ for the second oxygen concentration detecting element by using the label correction resistance $48_2$, followed execution of the steps 555 and 556 and then termination of the program.

Although in the first embodiment of the invention described above, two oxygen concentration detecting elements are used, the first embodiment is not limited to this, but also applicable in an $O_2$ sensor having a single detecting element corresponding to the upper detecting element shown in FIGS. 2 and 3.

Further, the differential amplifier circuit 47 may be omitted. Even if it is omitted, the above described correction of the circuit error such as the offset of the operational amplifier circuit 41 may be applied.

As described above, according the first embodiment of the invention, when the pumping current is zero, the output voltage of the operational amplifier circuit 41 is equal to the reference voltage of the non-inverting input terminal, and therefore the reference voltage is added to the voltage between the opposite ends of the pumping current detecting resistance 46 corresponding to the pumping current value. Therefore, a voltage accurately corresponding to the pumping current can be obtained even from a voltage infected with high level noise such as ignition pulse noise of the engine, since the voltage $V_{CENT}$ is much higher than the noise level. Further, by virtue of the construction that the voltage corresponding to the pumping current is obtained as a voltage corresponding to the difference between the output voltage of the operational amplifier circuit 41 and the voltage at the inverting input terminal of same, the above difference can accurately correspond to the actual pumping current, even if there occurs an error or a change in the reference voltage $V_{ERF}$, thereby accurately enabling to detect the pumping current.

Also, the respective electrodes of the cell element and the oxygen-pumping element arranged within the gas diffusion chamber are connected to each other within the gas diffusion chamber, x potential difference between the electrodes can be prevented, thereby preventing self-oscillation of the detected output and hence fluctuation in the output.

Further, since the difference between the output voltage $I_{PVW}$ and the inverting input terminal voltage $V_{CENT}$ is calculated after these voltages are converted to digital signals, converting error due to variations between converting reference voltages of A/D converters can be eliminated.

Furthermore, since a component in the output voltage which does not reflect the pumping current signal can be removed, the influences caused by such a circuit error as an $I_{PVN2}$ are proportional to the pumping current Ip, which are converted to respective digital signals by the A/D converter arranged within the input port 401 and are processed within the ECU 4.

Figure 8:
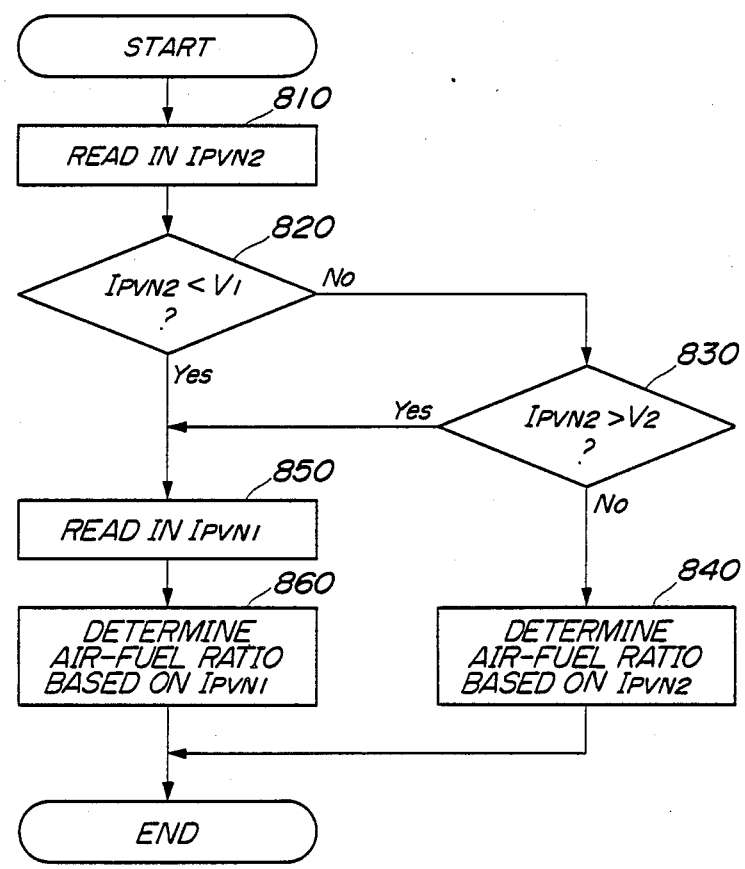
FIG. 8 is a flow chart to be executed by an ECU of the device of FIG. 8.

The ECU 4 executes a program shown in FIG. 8, in synchronism with the TDC signal. At a step 810, the digitalized voltage $I_{PVN2}$ is read in, and at the next step 820, it is determined whether or not the voltage $I_{PVN2}$ is smaller than a predetermined value $V_1$. If it is determined that the voltage $I_{PVN2}$ is equal to the value $V_1$ or larger than same, the program proceeds to a step 830, where it is determined whether the voltage $I_{PVN2}$ is larger than a second predetermined value $V_2 > (V_2 > V_4)$. If $V_1 \leq I_{PVN2} \leq V_2$, it is decided that the voltage $I_{PVN2}$ falls within the dynamic range of the differential amplifier, a range corresponding to circuit $47_2$. That is, the voltage $I_{PVN2}$ can show a proper value. Then the actual air-fuel ratio in the exhaust gases is detected on the basis of the voltage $I_{PVN2}$ (step 840). On the other hand, if $I_{PVN2} < V_1$ or $I_{PVN2} < V_2$, it is decided that the voltage $I_{PVN2}$ falls outside of the above range, and the digitalized voltage $I_{PVN1}$ is read in from the A/D converter at a step 850, whereby the air-fuel ratio is detected on the basis of the voltage $I_{PVN1}$ (step 860). The detection of the actual air-fuel ratio in the exhaust gases is effected, for example by reading a value of the air-fuel ratio corresponding to the determined voltage from a selected one of two different data maps to be used for the respective voltages $I_{PVN1}$ and $I_{PVN2}$. If the actual air-fuel ratio is equal to the stoichiometric ratio where the pumping current Ip is zero, the voltage $I_{PVW}$ becomes equal to the voltage $V_{CENT}$ so that the voltage $I_{PVN1}$ becomes equal, offset of the amplifier can be eliminated. Since this removal or correction is executed based on the actual circuit error detected when the pumping current is not supplied, the detection accuracy is further enhanced.

FIGS. 7 through 12 show second and third embodiments and variations of the third embodiment according to the invention. In FIGS. 7-12, like reference numerals designate elements and parts similar to those in FIGS. 2-6, and detailed description thereof is omitted.

Figure 7:
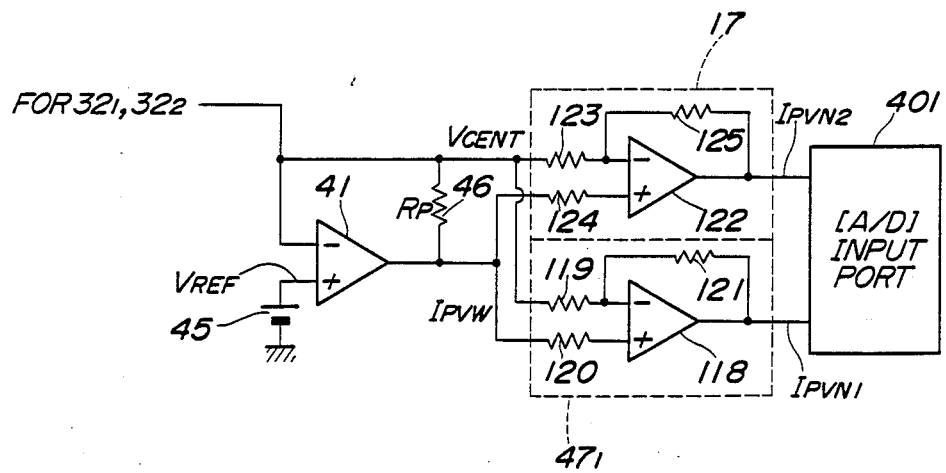
FIG. 7 is a circuit diagram of an oxygen concentration detecting device according to a second embodiment of the invention.

FIGS. 7 and 8 show the second embodiment of the invention, in which, instead of the single differential amplifier circuit 47 of the first embodiment, two differential amplifiers $47_1$ and $47_2$ are provided in order to detect the air-fuel ratio over a wider range as well as to enhance the detecting accuracy of the air-fuel ratio in the vicinity of the stoichiometric air-fuel ratio.

In FIG. 8, the differential amplifier circuit 47 in FIG. 2 comprises the two differential amplifiers $47_1$ and $47_2$, the respective values of resistances 119-121, 123-125 being set such that the amplification factor of the amplifier $47_2$ is larger than that of the amplifier $47_1$.

The inverting input terminal voltage $V_{CENT}$ and the output terminal voltage $I_{PVW}$ from the operationed amplifier circuit 41 are supplied to the differential amplifiers $47_1$ and $47_2$. The differential amplifier $47_1$ outputs a voltage $I_{PVN1}$ ($=I_{PVW} - V_{CENT}$), while the differential amplifier $47_2$ outputs a voltage $I_{PVN2}$ 5 times as high as the voltage ($I_{PVW} - V_{CENT}$). Since the pumping current Ip is obtained by the aforementioned equation (3), i.e. Ip = ($I_{PVW} - V_{CENT}$) / Rp, the voltages $I_{PVN1}$ and to the voltage $I_{PVN2}$, and each of the voltages $I_{PVN1}$ and $I_{PVN2}$ becomes zero volt.

The predetermined voltage values $V_1$ and $V_2$ are set such that $V_1 < 0$ volt, and $V_2 > 0$ volt in order for the voltage $I_{PVN1}$ to be applied to detection of the air-fuel ratio equal to or close to the stoichiometric ratio.

Although the present embodiment employs the oxygen concentration detecting sensor of the proportional-output type which has the oxygen-pumping element and the cell element, the invention is also applicable to a type other than this type, such as a threshold-current type in which the pumping-out of oxygen is effected only by the oxygen-pumping element, a reference oxygen region is formed at one of the electrodes of the oxygen-pumping element.

As described above, according to the second embodiment, the amplification factor of the voltage amplifying means is increased when the output voltage of the voltage amplifying means falls within a predetermined range corresponding to a stoichiometric air-fuel ratio and its vicinity, to a value larger than a value assumed when the output voltage falls out of the predetermined range, and the actual air-fuel ratio in the exhaust gases is determined on the basis of the output voltage of the voltage amplifying means. Therefore, the air-fuel ratio can be detected over a wide range, and at the same time, the accuracy of detection of the air-fuel ratio can be enhanced when the air-fuel ratio is in the vicinity of the stoichiometric ratio.

Also, if the output voltage of the voltage amplifying means is digitalized for calculation of the air-fuel ratio thereform it can be prevented that an output voltage is inputted to the A/D converter, which exceeds the maximum convertible voltage level.

Figure 9:
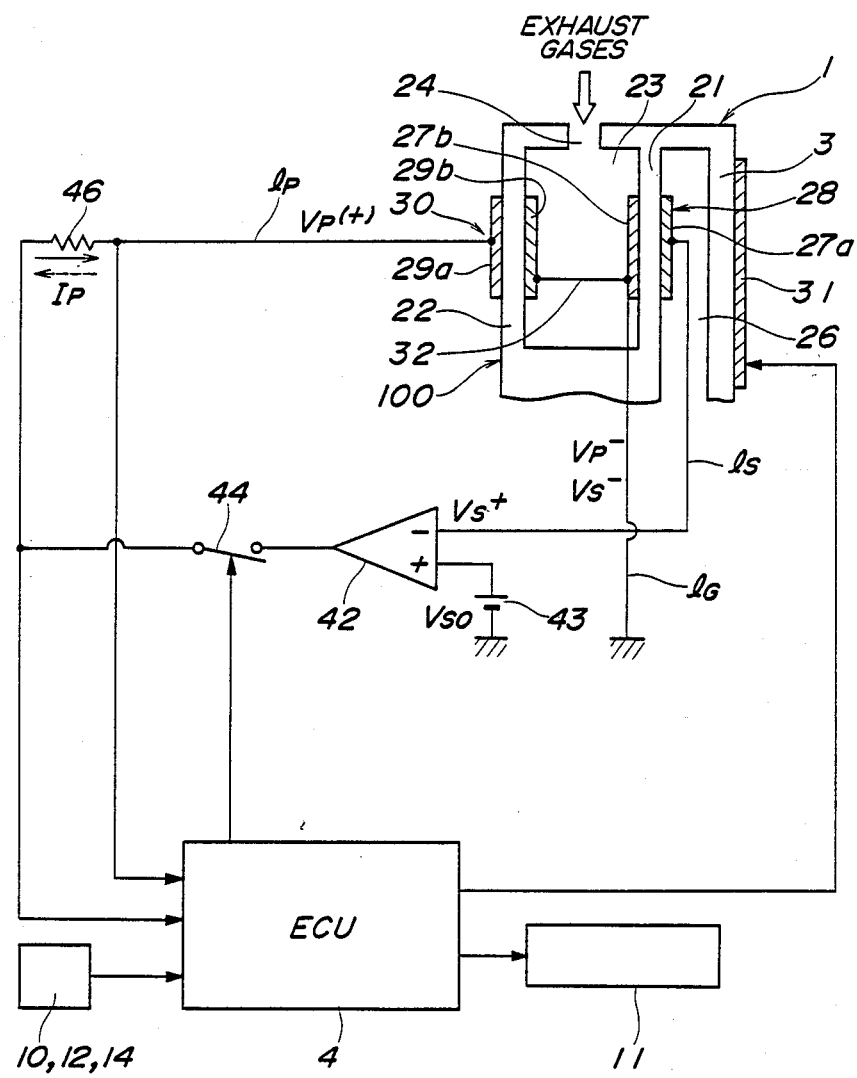
FIG. 9 is a schematic diagram of a third embodiment of the invention.

FIG. 9 shows a third embodiment of the invention.

This third embodiment is similar to the first embodiment in that the electrodes arranged within the gas diffusion chamber are connected to each other within the gas diffusion chamber by means of an electrically conduction member, but it is basically different from the first embodiment in that a lead wire $1_G$ extending from the electrically conductive member (which corresponds to the line 1 in the first embodiment) is grounded instead of being connected to the operational amplifier circuit etc., and only one oxygen concentration detecting element is provided.

That is, in the third embodiment, the operational amplifier circuit 41 and the differential amplifier circuit 47 are omitted, and a current detecting resistance 46 is connected between voltage applying means 42, 43 and an oxygen-pumping element 30 via a switch 44, similarly to the conventional arrangement. The voltages at the opposite ends of the resistance 46 are supplied to an ECU 4 to detect the pumping current from the supplied voltages, thereby determining the air-fuel ratio in the exhaust gases.

The electrodes 29b and 27b of the oxygen-pumping element 30 and a cell element 28 arranged within a gas diffusion chamber 23 are connected to each other by means of an electrically conductive member 32 within the gas diffusion chamber 23, and are grounded to the body of a vehicle via a leading wire $1_G$. Consequently, formation of a difference between potentials Vp− and Vs− at the respective electrodes 29b and 27b is prevented even when the leading wire 1G is disposed to extend to an electrical circuit such as the ECU 4 located at a long distance from the exhaust system of the engine with a sensor body 100 arranged therein.

Figure 10:
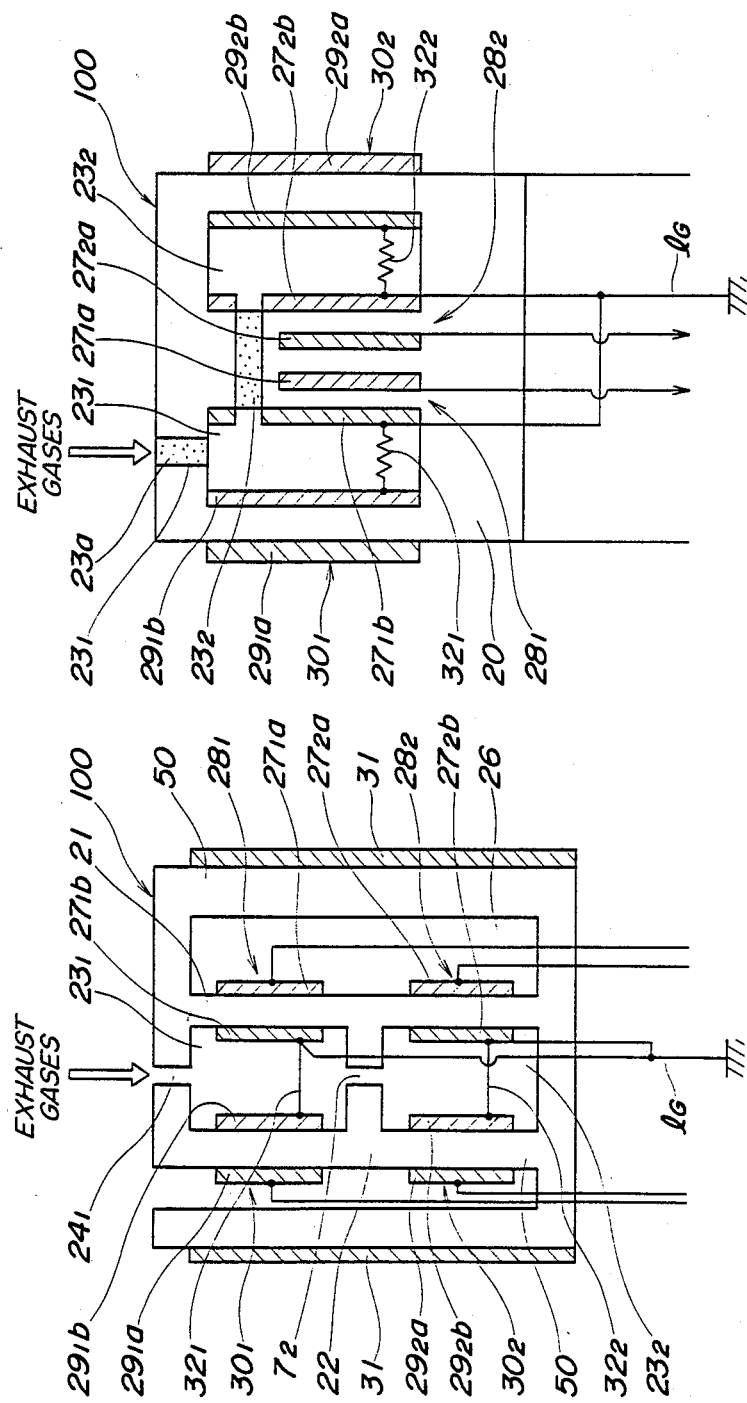
FIG. 10 is a cross sectional view of a variation of the of the oxygen concentration detecting device according to the third embodiment of the invention.

FIG. 10 shows a variation of the third embodiment, which differs from the third embodiment in that two oxygen concentration detecting elements are provided.

In the present variation, the electrodes $27_1b$ and $29_1b$ of a first oxygen-pumping element $30_1$ and a first cell element $28_1$ arranged within the gas diffusion chamber $23_1$ are connected to each other within the chamber $23_1$ by means of an electrically conductive member $32_1$, while also the electrodes $27_2b$ and $29_2b$ of a second oxygen-pumping element $30_1$ and a second cell element $28_1$ are connected to each other within a gas diffusion chamber $23_2$ by means of an electrically conductive member $32_2$. Therefore, similarly to the third embodiment, the respective pumping current is prevented from self-oscillation. Further, by virtue of connection of the electrodes $27_1b$ and $27_2b$ to the electrodes $27_2b$ and $29_2b$, the leading wires used for grounding can be reduced in number, thereby reducing the harness.

Figure 11:
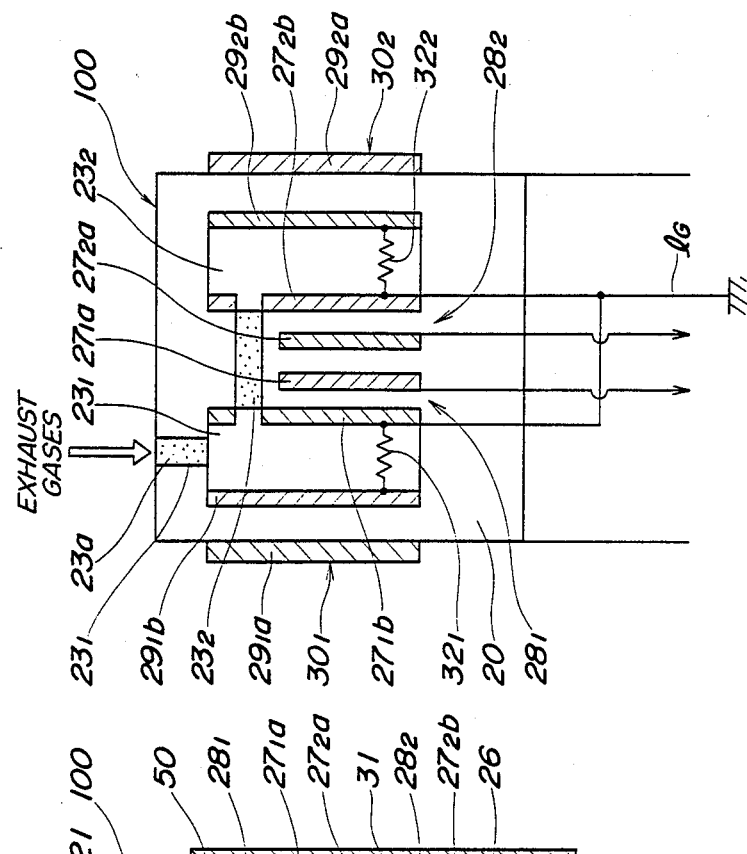
FIG. 11 shows a further variation of the device of FIG. 9.

FIG. 11 shows another variation of the third embodiment, which differs from the third embodiment in that two oxygen concentrating detecting elements are provided, which are arranged side by side, and that slits $24_1$ and $24_2$ are filled with oxygen-permeable members $24a$ and $24b$ filled for preventing entry of dust or the like. By selecting $24b$ to respective suitable values, flow resistance of the exhaust gases flowing into the chambers $23_1$ and $23_2$ through the slits $24_1$ and $24_2$ can be set to a suitable value.

Also in the present variation, the electrically conductive members $32_1$ and $32_2$ connect, respectively, the electrodes $27_1b$ and $29_1b$ and the electrodes $27_2b$ and $29_2b$ and ground them, thereby preventing self-oscillation and at the same time reducing the harness.

Figure 12:
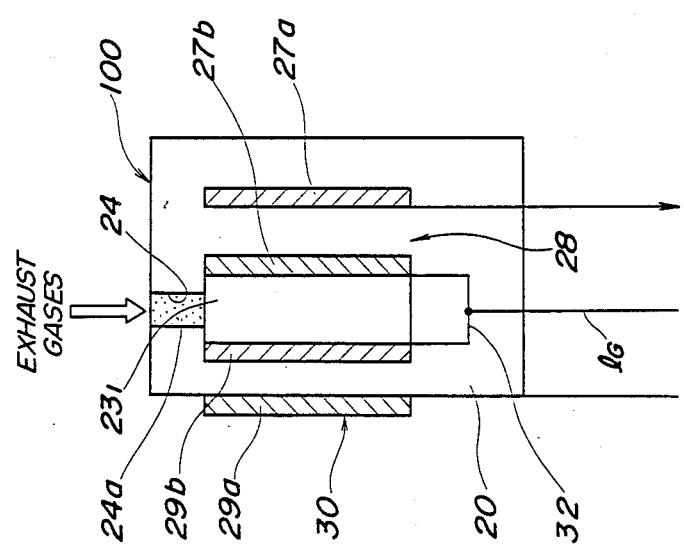
FIG. 12 shows another variation of the device of FIG. 10.

FIG. 12 shows another variation of the third embodiment, in which an electrically conductive member is not arranged within a gas diffusion chamber 23, but within the basic body 20 of a sensor 100 at a location other than the gas diffusion chamber 23 and the oxygen concentration detecting element.

Figure 13:
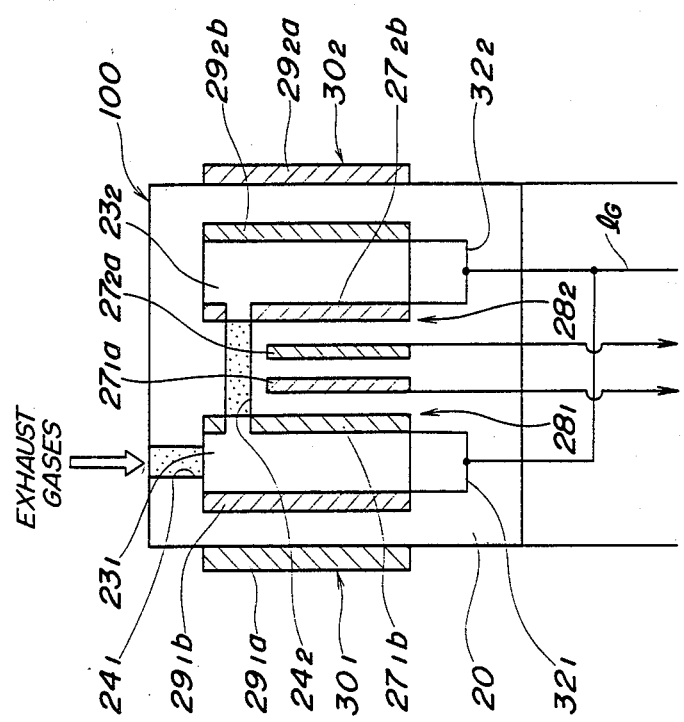
FIG. 13 shows still another variation of the device of FIG. 9.

FIG. 13 shows still another variation in which the arrangement of the electrically conductive member as shown in FIG. 12 is applied to the device with two oxygen concentration detecting elements arranged side by side.

Both variations of FIGS. 12 and 13 an provide effects similar to those of the variations of FIGS. 10 and 11.

What is claimed is:

1. In an oxygen concentration detecting device including at least one oxygen concentration detecting element formed by an oxygen-pumping element and a cell element, each of said oxygen-pumping element and said cell element being composed of a wall of a solid electrolytic material having oxygen ion-conductivity, and a pair of electrodes having said wall interposed therebetween, said oxygen-pumping element and said cell element defining a gas diffusion-limiting zone, a current detecting resistance connected in series to said oxygen-pumping element and cooperating therewith to form a series circuit, said current detecting resistance having a first end and a second end, voltage applying means for applying an output voltage corresponding to the difference between a voltage developed between said electrodes of said cell element and a first predetermined reference voltage to said series circuit formed by said oxygen-pumping element and said current detecting resistance, and output detecting means for outputting in the form of a voltage signal value of pumping current flowing through said current detecting resistance, the improvement comprising an operational amplifier circuit having a non-inverting input terminal supplied with a second predetermined reference voltage, an inverting input terminal connected to said first end of said current detecting resistance, and an output terminal connected to said second end of said current detecting resistance, and wherein said output detecting means detects a first voltage at said first end of said current detecting resistance and a second voltage at said second end of said current detecting resistance and outputs said voltage signal corresponding to the difference between the detected first and second voltages.

2. An oxygen concentration detecting device as claimed in claim 1, including converter means for converting said first voltage and said second voltage, respectively, to a first digital value and a second digital value, and calculating means for calculating the difference between said first and second digital values.

3. In an oxygen concentration detecting device including at least one oxygen concentration detecting element formed by an oxygen-pumping element and said cell element composed of a wall of a solid electrolytic material having oxygen ion-conductivity, and a pair of electrodes having said wall interposed therebetween, said oxygen-pumping element and said cell element defining a gas diffusion-limiting zone, a current detecting resistance being connected in series to said oxygen-pumping element and cooperating therewith to form a series circuit, said current detecting resistance having a first end and a second end, voltage applying means for applying an output voltage corresponding to the difference between a voltage developed between said electrodes of said cell element and a first predetermined reference voltage to said series circuit formed by said oxygen-pumping element and said current detecting resistance, and output detecting means outputting in the form of a voltage signal a value of pumping current for flowing through said current detecting resistance, the improvement comprising an operational amplifier circuit having a non-inverting input terminal supplied with a second predetermined reference voltage, an inverting input terminal connected to said first end of said current detecting resistance, and an output terminal connected to said second end of said current detecting resistance, and wherein said output detecting means includes correction means for correcting said voltage signal on the basis of said first voltage at said first end of said current detecting resistance and said second voltage at said second end of current detecting resistance which are obtained in a state where no pumping current is supplied to said current detecting resistance.

4. An oxygen concentration detecting device as claimed in claim 3, including heater means for heating said oxygen-pumping element and said cell element, and wherein said state where no pumping current is supplied includes a state where said heater means is inactivated.

5. An oxygen concentration detecting device as claimed in claim 3 or 4, including differential amplifier means for amplifying a difference between said first and second voltages, and wherein said correcting means corrects said voltage signal by a correction amount corresponding to a difference between said first voltage and the amplified difference from said amplifier means which are obtained in said state where no pumping current is supplied.

6. An oxygen concentration detecting device as claimed in claim 5, wherein said voltage signal is a difference between said amplified difference and a reference voltage of said first voltage, said correcting means subtracting said correction amount from said difference.

7. An oxygen concentration detecting device as claimed in claim 6, wherein said reference voltage of said first voltage is said first voltage obtained when said pumping current is zero and there exists no offset in said operational amplifier circuit.

8. An oxygen concentration detecting device as claimed in claim 5, wherein said correcting means corrects said voltage signal when said pumping current assumes a value falling within a predetermined small value range including zero.

9. In an air-fuel ratio detecting device for an internal combustion engine, said device being arranged in an exhaust system of the engine and including at least one oxygen concentration detecting element formed by an oxygen-pumping element and a cell element, each of said oxygen-pumping element and said cell element being composed of a wall of a solid electrolytic material having oxygen ion-conductivity, and a pair of electrodes having said wall interposed therebetween, current applying means for applying pumping current to said oxygen-pumping element to cause said pumping current to flow between said electrodes thereof, and controlling said pumping current to a value substantially proportional to the difference between actual oxygen concentration in exhaust gases from the engine and a predetermined reference value of the oxygen concentration, and signal generating means for generating a signal indicative of an air-fuel ratio of the exhaust gases corresponding to the controlled value of said pumping current, the improvement wherein said signal generating means comprises voltage generating means for generating an output voltage corresponding to the controlled value of said pumping current, voltage amplifying means for amplifying said output voltage from said voltage generating means, and determining means for increasing the amplification factor of said voltage amplifying means assumed when an output voltage from said voltage amplifying means falls within a predetermined range corresponding to a stoichiometric air-fuel ratio and its vicinity, to a value larger than a value assumed when said output voltage from said voltage amplifying means falls out of said predetermined range, and determining the air-fuel ratio in the exhaust gases from said output voltage from said voltage amplifying means.

10. An air-fuel ratio detecting device as claimed in claim 9, wherein said voltage amplifying means comprises a first voltage amplifier, and a second voltage amplifier having a larger amplification factor than that of said first voltage amplifier, said determining means determining the air-fuel ratio in the exhaust gases from an output voltage from said second voltage amplifier when said output voltage from said second voltage amplifier falls within a predetermined range, and determining the air-fuel ratio in the exhaust gases from an output voltage from said first voltage amplifier when said output voltage from said second voltage amplifier falls out of said predetermined range.

11. In an oxygen concentration detecting device for an internal combustion engine with an exhaust pipe, said device including a basic body having at least two walls formed of a solid electrolytic material having oxygen ion-conductivity, and at least one gas diffusion chamber defined therein, at least one oxygen concentration detecting element formed by an oxygen-pumping element and a cell element, said at least one oxygen concentration detecting element being arranged within said exhaust pipe, each of said oxygen-pumping element and said cell element being composed of a corresponding one of said walls, and a pair of electrodes with said corresponding wall interposed therebetween, one of said electrodes of said oxygen-pumping element and one of said electrodes of said cell element being arranged within said gas diffusion chamber and being connected to each other, voltage applying means for applying to said oxygen-pumping element a voltage corresponding to a difference between a voltage between said electrodes of said cell element and a predetermined reference voltage to cause pumping current to flow between said electrodes of said oxygen-pumping element, and output detecting means for converting said pumping current into a signal indicative of oxygen concentration, and outputting same, the improvement wherein said one of said electrodes of said oxygen-pumping element and said one of said electrodes of said cell element are connected to each other within said gas diffusion chamber.

12. In an oxygen concentration detecting device for an internal combustion engine with an exhaust pipe, said device including a basic body having at least two walls formed of a solid electrolytic material having oxygen ion-conductivity, and at least one gas diffusion chamber defined therein, at least one oxygen concentration detecting element formed by an oxygen-pumping element and a cell element, said basic body being arranged within said exhaust pipe, each of said oxygen-pumping element and said cell element being composed of a corresponding one of said walls, and a pair of electrodes with said corresponding wall interposed therebetween, one of said electrodes of said oxygen-pumping element and one of said electrodes of said cell element being arranged within said gas diffusion chamber and being connected to each other, voltage applying means for applying to said oxygen-pumping element a voltage corresponding to a difference between a voltage between said electrodes of said cell element and a predetermined reference voltage to cause pumping current to flow between said electrodes of said oxygen-pumping element, and output detecting means for converting said pumping current into a signal indicative of oxygen concentration, and outputting same, the improvement wherein said one of said electrodes of said oxygen-pumping element and said one of said electrodes of said cell element are connected to each other within said basic body at a location other than said gas diffusion chamber and said oxygen concentration detecting element.

* * * * *